US010620112B2

(12) United States Patent
Sambucetti et al.

(10) Patent No.: US 10,620,112 B2
(45) Date of Patent: Apr. 14, 2020

(54) MEASURING HIV RESERVOIRS WITH OPTICAL SCANNING

(71) Applicants: SRI INTERNATIONAL, Menlo Park, CA (US); THE TRUSTEES OF THE UNIVERSITY OF PENNSYLVANIA, Philadelphia, PA (US)

(72) Inventors: Lidia Sambucetti, Menlo Park, CA (US); Xiaohe Liu, Menlo Park, CA (US); Una O'Doherty, Philadelphia, PA (US)

(73) Assignees: SRI INTERNATIONAL, Menlo Park, CA (US); THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 134 days.

(21) Appl. No.: 15/654,661

(22) Filed: Jul. 19, 2017

(65) Prior Publication Data
US 2017/0322141 A1 Nov. 9, 2017

Related U.S. Application Data

(63) Continuation of application No. PCT/US2016/013813, filed on Jan. 19, 2016.

(60) Provisional application No. 62/105,067, filed on Jan. 19, 2015.

(51) Int. Cl.
G01N 15/14 (2006.01)
G01N 33/569 (2006.01)
G01N 33/50 (2006.01)
G01N 15/10 (2006.01)

(52) U.S. Cl.
CPC ..... G01N 15/1475 (2013.01); G01N 15/1429 (2013.01); G01N 15/1434 (2013.01); G01N 33/5094 (2013.01); G01N 33/56972 (2013.01); G01N 33/56988 (2013.01); G01N 2015/1006 (2013.01); G01N 2015/1488 (2013.01); G01N 2333/161 (2013.01); G01N 2333/70514 (2013.01)

(58) Field of Classification Search
CPC .......... G01N 15/1475; G01N 15/1429; G01N 33/5094; G01N 33/56972; G01N 15/1434; G01N 33/56988; G01N 2015/1006; G01N 2015/1488; G01N 2333/161; G01N 2333/70514
See application file for complete search history.

(56) References Cited

U.S. PATENT DOCUMENTS

| 7,277,569 | B2* | 10/2007 | Bruce ............... B82Y 5/00 382/128 |
| 2003/0151735 | A1 | 8/2003 | Blumenfield et al. |
| 2010/0168004 | A1* | 7/2010 | Williams ............. A61K 31/165 514/3.8 |
| 2011/0008417 | A1 | 1/2011 | Peut et al. |

OTHER PUBLICATIONS

Graf et al. Gag-Positive Reservoir Cells are Susceptible to HIV-Specific Cytotoxic T Lymphocyte Mediated Clearance In Vitro and Can Be Detected In Vivo (PLOS 8 (8): e71879, 1-14 (Aug. 2013).*
ISR-WO PCT/US16/13813, Mar. 18, 2016.

* cited by examiner

Primary Examiner — Gailene Gabel
(74) Attorney, Agent, or Firm — Ballard Spahr LLP

(57) ABSTRACT

Devices, systems and methods detect latent HIV in a patient on anti-retroviral therapy (ART), the method comprising using optical scanning to identify in a cell sample of the patient Gag+ CD4 downregulated cells as in indication of latent HIV.

13 Claims, No Drawings

MEASURING HIV RESERVOIRS WITH OPTICAL SCANNING

This application claims priority to Ser No. 62/105,067; filed Jan. 19, 2015.

This invention was made with government support under R21AI116216 and R01AI120011 awarded by the National Institutes of Health. The government has certain rights in this invention.

INTRODUCTION

There is need to detect latent HIV in infected individuals who don't have active infection, but have dormant HIV residing in HIV reservoirs. A major hurdle in HIV cure research is measuring HIV reservoir protein expression as well as HIV reservoir size. These measurements are challenging because of the small size of the reservoir, which is approximately one replication competent provirus in a million cells. While it is possible to measure HIV DNA in patients by PCR assays, most of the integrated HIV proviruses are hyper-mutated or contain massive deletions. Therefore, only a tiny fraction of the HIV DNA detected is replication competent and represents the true reservoir.

With the success of anti-HIV drug treatment, in many parts of the world HIV has become a chronic condition in which progression to AIDS may not occur. However, in order to manage HIV positive patients, especially with the rise of approaches to eradicate HIV, it is critical to be able to monitor the HIV reservoir that is capable of reactivating and causing disease.

Our invention detects reservoir cells that express HIV proteins using optical scanning to identify the Gag+ CD4 down-regulated cells. Once identified these cells can also be analyzed for other viral proteins markers and for HIV genetic markers by PCR. These additional markers can be used for further verification of intact HIV genomes and viruses with potential for reactivation. Moreover, optical scanning can distinguish replication competent from defective proviruses since multiple genes across the entire genome are required to generate a cell that expresses high levels of HIV Gag and downregulates CD4 (DeMaster et al JVI 2015).

A previous flow-cytometry-based assay used for analysis of Gag+ cells is costly and laborious (e.g. (Graf et al. PLoS One. 2013 Aug. 7; 8). Optical scanning allows for a higher-throughput and provides efficient secondary imaging to multiplex additional markers; however optical scanning was not previously considered because it was assumed that the reservoir expression was too low to be detected, particularly in patients on ART with no discernible viral load. We challenged this presumption and found that optical scanning had unexpected power and utility for identification of HIV Gag+ and can provide reliable identification of HIV reservoirs that express HIV proteins.

Relevant literature includes U.S. Pat. Nos. 7,113,624 and 7,277,569.

SUMMARY OF THE INVENTION

The invention provides methods to detect the expressed HIV reservoir (or detect cells that express HIV Gag and downregulate CD4 and/or detect HIV infected cells) in a patient in need thereof (having latent HIV infection or a reservoir of HIV infected cells), and particularly on antiretroviral therapy (ART); particularly by using optical scanning to identify in a cell sample of the patient Gag+ CD4 downregulated cells as in indication of the expressed HIV reservoir in the patient.

By reservoirs, we include cells that are considered latent, cells that are productively infected but return to resting state and thereby contribute to the reservoir. Latent cells are not currently releasing infectious virions, but capable of producing infectious virions upon perturbation. HIV reservoir cells persist on antiviral therapy over years and contribute to reservoir persistence.

In embodiments: the optical scanning is selected from: fiber-optic array scanning (e.g. Das et al., 2012, Lung Cancer 77:421-426), laser scanning microscopy (cytometry) (e.g. Tarnok et al, 2002, Cytometry (Clinical Cytometry) 50:133-43) automated digital microscopy (e.g. Bauer et al. 2000, Clin Cancer Res 6 3552-9) and high content screening (analysis) instrumentation (e.g. Zanella et al., 2010 Trends in Biotechnol 28 (5) 237-45);

the patient has experimentally undetectable viral load (<25, <50 or, <75 copies/ml);

the patient patients had been on ART for at least one (or two) years;

the sample comprises PBMCs of the patient, adhered to a side, fixed and permeabilized and stained for CD4 and intracellular GAG;

the method further comprises assigning positional coordinates to one or more of the cells;

the method further comprises isolating one or more of the cells, e.g. for secondary molecular or marker analysis;

the method further comprises a secondary analysis of one or more of the cells that is quantifying multiplexed fluorescent makers by fluorescent microscopy;

the method further comprises a secondary analysis of one or more of the cells that is genetic analysis of the cell or of the HIV;

the method further comprising a secondary analysis of one or more of the cells that define in more detail the proteins that are expressed such as additional HIV proteins (e.g. Nef) or cellular surface receptors that define the cells phenotype; and/or the method comprises mounting a slide comprising cells of the sample on a fiber optic array scanner and fluorescent imaging the cells to detect Gag+, CD4− cells.

In embodiments the scanner comprises:

an imager stage having a planar surface for supporting a sample comprising the slide;

a bifurcated light path having two fiber optic bundles, each bundle having a first end arranged to define an input aperture for viewing the sample on the imager stage, and a distal bundle end arranged to define an output aperture disposed away from the imager stage;

a scanning source arranged to scan a beam along a path that is perpendicular to the sample on the imager stage and closely adjacent to both bundles of the bifurcated light path such that a substantially circular spot of illumination provided by the scanning source on the imager stage sample provides a light signal at least a portion of which is received by the input aperture of each bundle and transmitted via the bifurcated light path to the output aperture;

a photodetector arranged to detect the light signal at the distal end; and a processor that processes the light signal detected by the photodetector.

In embodiments the method comprises:
supplying a substantially circular beam of radiation perpendicular to the sample;
maintaining the perpendicular direction of the radiation beam as it sweeps along a scan path on the sample;
reflecting at least some light produced by beam interaction with the sample in a direction away from the sample;
collecting light produced by beam interaction with the sample in at least one proximate element of an array of fiber optic first ends;
detecting collected light at a selected output region; and
coordinating sweeping, moving and detecting to generate an array of picture elements representative of at least a portion of the sample.

In further embodiments:
counting Gag+CD4negative cells by FAST provides a correlate of reservoir size because to express Gag at high levels and down regulate CD4 requires that Gag, tat, rev, Nef and probably Env are intact; this spans most of the HIV genome;
counting Gag+CD4negative after exposure to a latency reversal agent (in vitro and in vivo) provides a method to determine the potency of a latency reversal agent to enhance expression from integrated HIV DNA;
counting Gag+CD4negative after exposure to a mixture of potent latency reversal agents provides a method to measure reservoir size directly as an alternate to laborious Quantitative Viral Outgrowth Assay (QVOA) assay; and/or
the FAST method may also be used for simply measuring the frequency of cells that express HIV proteins from both defective and replication competent virus.

In further embodiments the invention provides:
a diagnostic method to measure reservoir size;
a method to monitor efficacy of therapeutic interventions to reduce reservoir size. A diagnostic method to show efficacy of therapies that target HIV reservoirs; and/or
a method to monitor efficacy of latency reversal agents to enhance reservoir expression.

The invention specifically provides all combinations of the recited embodiments, as if each had been laboriously individually set forth.

DETAILED DESCRIPTION OF PARTICULAR EMBODIMENTS AND EXAMPLES THEREOF

A reservoir of infected cells exists in HIV-infected patients on anti-retroviral therapy (ART) that leads to rebound of viremia when ART is stopped and remains an important barrier to HIV cure (1-3). The majority of proviruses found in ART patients are hypermutated or contain large deletions that render these proviruses defective for replication (4). Proviruses carrying large deletions are generally not thought to be expressed at levels sufficient to detect HIV protein expression by immunofluorescence since the viral genes tat and rev, which are required for efficient transcription and export of viral RNAs (5-11), are often missing or mutated (4, 12).

While the reservoir is frequently described as transcriptionally silent, several studies suggest that a portion of the HIV reservoir may be transcriptionally active in ART patients in vivo (13, 14, 15). Notably, up to 10% of cells containing HIV DNA appear to contain viral RNA that can be detected with primers to the gag region (16). In contrast, tat/rev multiply spliced RNA (msRNA) forms were detected at much lower frequency (16). We have studied HIV expression in an in vitro model of latency that involves direct infection of primary resting CD4+ T cells in which viral spread is undetectable. Consistent with in vivo data from Fischer et al., we find that gag unspliced RNA (usRNA) is the predominant viral transcript in resting CD4 T cells infected in vitro, whereas tat/rev msRNA is present at much lower levels (17). We extended this work with the novel finding that Gag appears to be expressed in a fraction of infected, resting T cells. Moreover, we found tantalizing evidence that a low frequency of cells also express Gag protein in vivo in patients on ART (18).

We began by conducting experiments in our in vitro model of latency (17, 18) to better define the specificity of our Gag staining and to further characterize the Gag+ cells. We discovered that the Gag+ cells had a unique CD4-CD8- "double negative" T cell phenotype, and we went on to show that similar cells exist in patient samples. Thus, Gag+ double negative (DN) T cells may provide a unique phenotype for identifying infected cells that express HIV proteins.

Fiber-optic array scanning technology: Patient cells were thawed, centrifuged once and resuspended in 3 mls of PBS. NL4-3 infected cells were cultured for 3 days post-infection, collected, centrifuged, and resuspended in 3 mls of PBS. Approximately, 20 million patient PBMCs or NL4-3-infected CD4+ T cell cultures were allowed to adhere for 40 minutes at 37° C. in 100% humidity on pre-treated slides. Cells were fixed, permeabilized and stained with KC57, mouse anti-human CD4 Alexa 647 or TCR α/β, and DAPI nuclear stain. Each slide of immunolabeled cells was scanned and fluorescence emission from labeled cells was collected in an array of optical fibers forming a wide collection aperture. Cells that had a ratio of average wavelength intensity to target wavelength intensity greater than one were considered to be autofluorescent and were excluded by the FAST algorithm filters. Potential "hits" for Gag- expressing cells were localized to an accuracy of 40 microns by the FAST scan and then reimaged using an automated digital microscope with a 20× objective. Manual image review was performed for each positive "hit", and debris and dye aggregates were further excluded based on morphology. To quantify the total number of PBMCs per slide, Thermo Scientific Cellomics Array VT was used to count DAPI+ nuclei.

Resting CD4 T Cells Express Gag Protein After Direct Infection In Vitro

We previously described Gag protein signal in our in vitro model of directly infected resting CD4 T cells. We were convinced of the quiescent nature of the infected cells since they lacked activation markers and included cells that are phenotypically naïve (17). We interpreted our results initially to represent de novo protein expression (17); however, it was possible that the Gag signal originated from bound, unfused virions (19). For example, rare, activated, and productively infected cells could release virions that bind to nearby uninfected resting CD4 T cells giving a false appearance that could be mistaken for nascent expression from a resting cell. In addition, expression from unintegrated HIV DNA has also been reported and could give rise to Gag+ cells (31). To address if detection of Gag represented de novo translation from an integrated provirus, we set out to determine if sorted Gag+ cells contained integrated HIV DNA. We reasoned that enrichment of integrated HIV DNA in Gag+ cells sorted by FACS (relative to Gag− cells) would signify protein expression from integrated HIV DNA in infected cells. If, however, the Gag signal were an artifact of bound virions, we would expect Gag+ cells to be enriched for HIV RNA, but not integrated HIV DNA.

Quiescent CD4+ T cells in the G0/1a stage of the life cycle were enriched by depletion of lineage and activation markers (39, 40). Cells were infected with NL4-3 by spinoculation (32) and cultured in the absence of activating cytokines and in the presence of the protease inhibitor saquinavir (17, 39). dNs were added to infected cultures to overcome SAMHD1− mediated restriction that has been described in resting T cells (33, 41, 42). Three days postinfection cells were stained with LIVE/DEAD aqua and stained for surface markers with antibodies against CD3 (AF700), CD4 (PECy5.5), and CD25/CD69/HLA-DR (APC). Cells were then fixed, permeabilized and stained for HIV Gag. Surprisingly, we found that the Gag+ cells expressed surface CD3 but were negative for CD4 after direct infection. Consistent with our previous work, the cultured Gag+ cells lacked the activation markers CD25, CD69 and HLA-DR at day 3. Notably CD4+ T cells cultured in the absence of antigen presenting cells and cytokines have lower levels of TCR-ζ chain phosphorylation suggesting the process of culturing cells results in a lower activation state (43). The level of integrated HIV DNA was determined to be 0.32 copies per cell in the bulk culture (termed whole culture, WC). Gag+CD4− cells contained 1.2 HIV proviruses per cell, which represented an enrichment of integrated HIV DNA in Gag+CD4− cells compared to Gag− cell populations (Gag−CD4− cells contained 0.013 copies, Gag−CD4int cells contained 0.11 copies, and Gag− CD4+ cells contained 0.24 copies of integrated HIV DNA per cell). The enrichment of integrated HIV DNA among the Gag+ cells indicates that the detected Gag signal reflects de novo protein expression and not bound virions. Furthermore, cells cultured in the presence of the integrase inhibitor raltegravir had very low Gag staining, indicating that Gag signal was enhanced with viral integration.

Gag+CD4− Cells are α/β Cells

The infected, Gag+ cells lacking surface CD4 (above) warranted further investigation. To further characterize the Gag+CD4− T cells, we performed surface marker phenotyping. Direct infection with the X4-tropic NL4-3 was performed as above. The resulting infection yielded a culture in which ~10% of cells had a Gag+CD4− phenotype suggesting that surface CD4 was lost during the 3 day culture period. Gag+CD4− cells expressed surface T cell receptor α/β and were negative for T cell receptor γ/δ, CD8, CD11c, CD14, and CD16/CD56. Importantly, cells infected with the primary R5-tropic isolate CH058 (44) showed similar phenotype. Given that the process of HIV fusion utilizes CD4, it is likely that the identified Gag+CD4− cells were indeed, at one time, genuine CD4+ T cells.

To confirm the FACS observations by imaging, cells from infected cultures were plated on glass slides, and antibodies against CD4 and Gag were added after fixation and permeabilization. Fiber-Optic Array Scanning Technology (FAST) (45) was used to image cells positive for HIV Gag and CD4. Merged images of CD4 and Gag staining were generated uniquely for cells that stained positive for Gag. We identified Gag+ cells with punctate intracellular CD4 staining. The punctate CD4 staining pattern was unique to Gag+ cells. The lack of surface CD4 by FACS and the punctate staining pattern by FAST are consistent with internalized CD4 in Gag+ cells.

Viral protein expression is responsible for CD4 internalization in infected resting cells.

Our results suggested that the lack of surface CD4 was related to expression of viral proteins. However, incoming virions might also induce this phenotype. For example, HIV Env on incoming virions might mask CD4 on the cell surface or crosslinking of CD4 by HIV Env might induce CD4 internalization. To test whether infection alone could cause the CD4− phenotype, we used the gutted gene therapy vector VRX1090 (26), which lacks viral genes and was engineered to express GFP driven by the EF1α promoter in infected cells. Resting CD4+ T cells were infected with VRX1090 that was pseudotyped with X4 HIV Env (LAI) and cultured in the absence or presence of the integrase inhibitor raltegravir, and GFP expression was evaluated on day 3 post-infection. Infected cells that expressed GFP had wild-type levels of surface CD4, suggesting that infection alone with an HIV Env-pseudotyped virus did not lead to CD4 internalization. Moreover, these data suggested that viral gene expression is required for CD4 internalization in resting cells.

Given that multiple viral proteins (Vpu, Env, Nef) can lower levels of surface CD4 (46-53), we strongly suspected that other viral proteins besides Gag were expressed in these infected resting T cells. To dissect which viral proteins contribute to loss of surface CD4 in our system, we performed infections of resting cells with either wild-type 89.6 virus or 89.6 viruses lacking vpu, nef or env (22, 23). Mutations in nef and env alone resulted in intermediate levels of surface CD4, while virus carrying a mutation in the vpu gene showed nearly complete loss of surface CD4, a similar phenotype to wild type virus. Our experiments suggest that de novo synthesis of Env and Nef likely contributed to the CD4 downregulation phenotype.

We previously showed that directly infected resting CD4 T cells expressed very low levels of Env (17), but we had not addressed whether Nef could be expressed in resting cells after direct infection. To determine if Nef was also expressed, we infected cultures with NL4-3-IRES-GFP, which expresses GFP from nef msRNA transcripts (54). We detected GFP expression in resting cells indicating Nef expression on day 3 post-infection. This is consistent with high levels of nef msRNA reported in other direct infection models (55-57). Notably, the cells expressing Nef/GFP also lacked surface CD4.

Defective proviruses can express low levels of HIV protein in the absence of tat/rev, but may not completely downregulate CD4.

Given the important roles of Tat and Rev to enhance viral gene expression (reviewed in (11, 58)), we were surprised by the relatively high levels of HIV Gag in the apparent absence of tat/rev msRNA in our infected resting cells (17). However, it was possible that tat/rev msRNA was present but not detected in our system; thus, we asked whether these genes were required for LTR-driven viral gene expression by infecting resting cells with viruses lacking the tat/rev genes in our in vitro system. Resting CD4+ T cells were infected by spinoculation with Env-pseudotyped virions containing the viral vector VRX494 (25), which lacks the tat, rev, vif, vpr, vpu, and nef genes, but contains the HIV LTR promoter and an ORF that encodes GFP and viral genetic elements necessary for reverse transcription and integration.

Three days post-infection, a subset of infected cells (3%) expressed low levels of GFP, demonstrating that basal LTR-driven expression of viral genes was detectable in the absence of HIV accessory proteins (11, 58). This was above the background frequency of GFP+ cells detected in the cells cultured in the presence of raltegravir. Unintegrated HIV DNA is not expected to contribute to expression in this experiment since Vpr is required for expression from unintegrated HIV DNA, and because we assayed early after infection before expression from unintegrated HIV DNA occurs (28). Thus, we can detect proviral gene expression in resting CD4 T cells without tat/rev.

The low-level expression of GFP in resting cells infected with lentiviral vector lacking tat/rev and all other HIV accessory proteins raises the question of whether defective proviruses could be expressed in CD4+ T cells. This has clinical implications in light of the predominance of defective proviruses in HIV infected individuals. We next asked whether proviruses with a mutation in tat could express viral proteins. We chose to use NLENG1-IRESΔtat, a sensitive reporter virus that contains a GFP cassette inserted upstream of the nef gene and a stop codon after the first 18 amino acids of Tat. Resting cells were infected with NLENG1-IRESΔtat and its parent virus, and GFP expression and CD4 levels were measured 5 days post-infection. GFP+ cells were detected in cultures infected with NLENG1-IRES (59) and NLENG1-IRESΔtat; however, the mode level of GFP expression was 28 fold lower in cells infected with NLENG1-IRESΔtat compared to the parent NLENG1-IRES virus. Thus, Tat transactivates HIV-1 expression in resting CD4 T cells even though we failed to detected it by RT-PCR (17). Nonetheless, cells infected with NLENG1-IRESΔtat expressed low levels of viral protein, again indicating a detectable level of basal or Tat-independent transcription. Parallel, infected cultures were fixed and stained for intracellular Gag. Though fixation reduced GFP fluorescence by an order of magnitude (31), Gag+GFP+ cells were readily detected in cultures infected with the parent virus that expressed wild-type Tat (NLENG1-IRES). In addition to GFP, there is a suggestion that Gag may also be expressed with NLENG1-IRESΔtat though the levels are very near background, suggesting that Gag expression may occur at low levels in the absence of Tat.

To determine if proviruses with large deletions in the tat/rev/env region can express detectable viral Gag in quiescent CD4 T cells, we generated a mutant NL4-3 virus with a deletion between nucleotides 5743 to 7250. The resulting virus, NL43Δ5743-7250, was similar to proviruses reported recently by Ho et al (4). We then infected resting CD4+ T cells by spinoculation using X4-tropic Env-pseudotyped NL43Δ5743-7250 virions and cultured the cells for three days. In three independent experiments, we consistently found very low levels of Gag just above the background levels as assessed by an integrase inhibitor, raltegravir control. Taken together, our results with sensitive reporter viruses suggest that very low-level expression of viral proteins can occur in resting cells infected with defective proviruses that contain deletions in the region of tat/rev/env. However, flow assays to detect Gag expression from Tat mutants are near background and thus distinguishable from replication competent HIV. These findings may have important implications for immune eradication strategies and methods to monitor them. Notably, low-level protein expression from defective proviruses could be visible to the primed immune system.

FAST Can Identify Gag+ Cells Present at Low Frequency

The FAST (Fiber-optic Array Scanning Technology) platform is an alternative method for the identification of rare cells using fluorescent detection and laser scanning technology (45). What distinguishes FAST from other cell-phenotyping techniques is its scanning speed that enables the quantitative analysis of 20 million cells per minute. Since FAST is performed on standard microscopy slides, an automated digital microscope systematically performs fluorescent imaging on each putative rare cell and is capable of analyzing up to 6 fluorophores. Thus, all rare events can be visualized and efficiently recorded with highresolution microscopy.

Since FAST provides an independent technology for the identification of rare cells as well as image-based verification, we were interested to determine if FAST could detect HIV-infected cells that express viral proteins in a patient on ART. As a proof of principle experiment, resting CD4 T cells were infected in vitro and serially diluted in a background of uninfected PBMCs to create cultures with progressively lower levels of Gag+ cells. In an initial experiment both flow cytometry and FAST were used to identify and quantify Gag+ cells in the diluted samples. We found good agreement between flow cytometry and FAST showing that FAST could reproducibly detect Gag+ cells down to a frequency of 0.4 Gag+ cells per million PBMCs. Notably, the dim and internalized CD4 staining shown above provided additional specificity for Gag signals detected by FAST, as Gag+ cells generally had lower CD4 levels and often showed punctate CD4, consistent with Env-mediated or Nefmediated CD4 internalization and degradation. To determine the accuracy of measuring the frequency of Gag+ cells by FACS, we made serial dilution of NL4-3-infected cultures and measured HIV DNA in sorted Gag+CD4− cells. We found that FACS did not count Gag+ cells accurately at low frequencies. For instance, when we diluted 100 Gag+ CD4− cells per million PBMCs, we found that 100% of sorted Gag+CD4− cells contained HIV DNA.

However, when we diluted 10 Gag+CD4− cells per million PBMCs we found only 22% of the cells contained integrated HIV DNA, assuming 1 genome per cell. This is an expected limitation of flow cytometry because Gag− cells are occasionally present in the same droplet as Gag+ cells and are sorted together, which results in a decrease of HIV DNA per sorted cell, an effect that is especially apparent at low target frequencies. Thus, FACS is a tedious, error-prone method to quantify HIV reservoirs that express proteins. On the other hand, each initial "hit" detected by FAST is confirmed by imaging indicating it would be less susceptible to spurious background event, and FAST technology provides more robust high-throughput measurements.

FAST Can be Used to Identify HIV-Infected Cells that Express Viral Proteins in Patients Because each initial "hit" by FAST is confirmed by imaging, FAST is less susceptible to spurious background events that complicate the quantitation of Gag+ cells at low frequencies by FACS. To explore the potential of FAST, we asked if Gag+ cells could be identified in HIV infected individuals on ART. PBMCs from ART patients were adhered to slides, fixed, permeabilized and stained for CD4 and intracellular Gag. Six representative images of Gag+ cells that have undetectable levels of CD4 are shown. These patients had been on ART for at least two years and had undetectable viral loads at the time of sampling (<50 copies/ml). While the majority of Gag+ cells were CD4−, some Gag+, CD4+ cells were identified. The pattern of CD4 staining ranged from nearly wild-type levels to barely detectable and punctate (ARTS).

We wanted to determine if the cells that expressed HIV Gag in vivo were analogous to the cells we studied in vitro. Thus, we tested if these cells also expressed TCRα/β as in our in vitro system. We stained a replicate slide from the same ART patient with antibodies against HIV Gag, CD4, and TCRα/β. We show three cells that expressed HIV Gag that also expressed TCRα/β, while lacking CD4. In total, we found 12 Gag+ cells, all of which were TCRα/β positive. Notably, Gag+TCRα/β+ cells are present at a frequency comparable to our previous studies that utilized a cell sorting approach to estimate the frequency of resting T cells that expressed HIV proteins (18). In this context, these Gag+ TCRα/β+ cells represent HIV infected T cells that are expressing HIV proteins and thus internalize CD4.

Gag+CD4− cells and Gag+CD4+ cells were counted and frequencies were determined by dividing the number of nuclei examined per slide. The percentage of proviruses expressing Gag was determined by dividing the number of Gag+ cells per million PBMCs by the number of integrated HIV proviruses per million PBMCs and multiplying by 100. Gag+ cells, which were mostly CD4−, persisted over a period of 5 years in one patient and were detectable in all 5 patients that were assayed. Our FAST studies in patients' cells indicate that Gag+ cells contribute to the HIV reservoir and that FAST is a useful method for the direct measurement of HIV expression.

REFERENCES

1. Finzi, D., J. Blankson, J. D. Siliciano, J. B. Margolick, K. Chadwick, T. Pierson, K. Smith, J. Lisziewicz, F. Lori, C. Flexner, T. C. Quinn, R. E. Chaisson, E. Rosenberg, B. Walker, S. J. Gange, J. Gallant, and R. F. Siliciano. 1999. Latent infection of CD4+ T cells provides a mechanism for lifelong persistence of HIV-1, even in patients on effective combination therapy. Nat Med 5:512-517.
2. Chun, T. W., L. Carruth, D. Finzi, X. Shen, J. A. DiGiuseppe, H. Taylor, M. Hermankova, K. Chadwick, J. Margolick, T. C. Quinn, Y. H. Kuo, R. Brookmeyer, M. A. Zeiger, P. Barditch-Crovo, and R. F. Siliciano. 1997. Quantification of latent tissue reservoirs and total body viral load in HIV-1 infection. Nature 387:183-188.
3. Wong, J. K., M. Hezareh, H. F. G √°nthard, D. V. Havlir, C. C. Ignacio, C. A. Spina, and D. D. Richman 1997. Recovery of replication-competent HIV despite prolonged suppression of plasma viremia. Science 278:1291-1295.
4. Ho, Y. C., L. Shan, N. N. Hosmane, J. Wang, S. B. Laskey, D. I. Rosenbloom, J. Lai, J. N. Blankson, J. D. Siliciano, and R. F. Siliciano. 2013. Replication-competent noninduced proviruses in the latent reservoir increase barrier to HIV-1 cure. Cell 155:540-551.
5. Cullen, B. R. 1990. The HIV-1 Tat protein: an RNA sequence-specific processivity factor? Cell 63:655-657.
6. Sodroski, J. G., C. A. Rosen, and W. A. Haseltine. 1984. Trans-acting transcriptional activation of the long terminal repeat of human T lymphotropic viruses in infected cells. Science 225:381-421.
7. Laspia, M. F., A. P. Rice, and M. B. Mathews. 1989. HIV-1 Tat protein increases transcriptional initiation and stabilizes elongation. Cell 59:283-292.
8. Fisher, A. G., M. B. Feinberg, S. F. Josephs, M. E. Harper, L. M. Marselle, G. Reyes, M. A. Gonda, A. Aldovini, C. Debouk, R. C. Gallo, and et al. 1986. The trans-activator gene of HTLV-III is essential for virus replication. Nature 320:367-371.
9. Dayton, A. I., J. G. Sodroski, C. A. Rosen, W. C. Goh, and W. A. Haseltine. 1986. The trans-activator gene of the human T cell lymphotropic virus type III is required for replication. Cell 44:941-947.
10. Malim, M. H., J. Hauber, S.-Y. Le, J. V. Maizel, and B. R. Cullen. 1989. The HIV-1 rev trans-activator acts through a structured target sequence to activate nuclear export of unspliced viral mRNA. Nature 338:254-257.
11. Karn, J., and C. M. Stoltzfus. 2012. Transcriptional and posttranscriptional regulation of HIV-1 gene expression. Cold Spring Harbor perspectives in medicine 2:a006916.
12. Yukl, S., S. Pillai, P. Li, K. Chang, W. Pasutti, C. Ahlgren, D. Havlir, M. Strain, H. Gunthard, D. Richman, A. P. Rice, E. Daar, S. Little, and J. K. Wong. 2009. Latently-infected CD4+ T cells are enriched for HIV-1 Tat variants with impaired transactivation activity. Virology 387:98-108.
13. Furtaldo, M. R., D. S. Callaway, J. P. Phair, B. S. Kunstman, J. L. Stanton, C. A. Macken, A. S. Perelson, and S. M. Wolinsky. 1999. Persistence of HIV-1 transcription in peripheral blood mononuclear cells in patients receiving potent antiretroviral therapy. New England Journal of Medicine 340:1614-1622.
14. Lewin, S. R., M. Vesana, and L. Kostrikis. 1999. Use of real-time PCR and molecular beacons to detect virus replication in Human Immunodeficiency Virus type 1-infected individuals on prolonged effective antiretroviral therapy. Journal of Virology 73:6099-6103.
15. Patterson, B. K., S. McCallister, M. Schutz, J. N. Siegel, K. Shults, Z. Flener, and A. Landay. 2001. Persistence of intracellular HIV-1 mRNA correlates with HIV-1-specific immune responses in infected subjects on stable HAART. AIDS 15:1635-1641.
16. Kaiser, P., B. Joos, B. Niederost, R. Weber, H. F. Gunthard, and M. Fischer. 2007. Productive Human Immunodeficiency Virus Type 1 Infection in Peripheral Blood Predominantly Takes Place in CD4/CD8 Double-Negative T Lymphocytes. J Virol 81:9693-9706.
17. Pace, M. J., E. H. Graf, L. M. Agosto, A. M. Mexas, F. Male, T. Brady, F. D. Bushman, and U. O'Doherty. 2012. Directly infected resting CD4+ T cells can produce HIV Gag without spreading infection in a model of HIV latency. PLoS Pathog 8:e1002818.
18. Graf, E. H., M. J. Pace, B. A. Peterson, L. J. Lynch, S. B. Chukwulebe, A. M. Mexas, F. Shaheen, J. N. Martin, S. G. Deeks, M. Connors, S. A. Migueles, and U. O'Doherty. 2013. Gag-Positive Reservoir Cells Are Susceptible to HIV-Specific Cytotoxic T Lymphocyte Mediated Clearance. PLoS One 8:e71879.
19. Saleh, S., F. Wightman, S. Ramanayake, M. Alexander, N. Kumar, G. Khoury, C. Pereira, D. Purcell, P. U. Cameron, and S. R. Lewin. 2011. Expression and reactivation of HIV in a chemokine induced model of HIV latency in primary resting CD4+ T cells. Retrovirology 8:80.
20. Dahabieh, M. S., M. Ooms, V. Simon, and I. Sadowski. 2013. A doubly fluorescent HIV-1 reporter shows that the majority of integrated HIV-1 is latent shortly after infection. Journal of virology 87:4716-4727.
21. Bullen, C. K., G. M. Laird, C. M. Durand, J. D. Siliciano, and R. F. Siliciano. 2014. New ex vivo approaches distinguish effective and ineffective single agents for reversing HIV-1 latency in vivo. Nat Med 20:425-429.
22. Collman, R., J. W. Balliet, S. A. Gregory, H. Friedman, D. L. Kolson, N. Nathanson, and A. Srinivasan. 1992. An infectious molecular clone of an unusual macrophage-tropic and highly cytopathic strain of human immunodeficiency virus type 1. Journal of virology 66:7517-7521.
23. Balliet, J. W., D. L. Kolson, G. Eiger, F. M. Kim, K. A. McGann, A. Srinivasan, and R. Collman 1994. Distinct effects in primary macrophages and lymphocytes of the human immunodeficiency virus type 1 accessory genes vpr, vpu, and nef: mutational analysis of a primary HIV-1 isolate. Virology 200:623-631.
24. Carter, C. C., A. Onafuwa-Nuga, L. A. McNamara, J. t. Riddell, D. Bixby, M. R. Savona, and K. L. Collins. 2010. HIV-1 infects multipotent progenitor cells causing cell death and establishing latent cellular reservoirs. Nat Med 16:446-451.
25. Humeau, L. M., G. K. Binder, X. Lu, V. Slepushkin, R. Merling, P. Echeagaray, M. Pereira, T. Slepushkina, S. Barnett, L. K. Dropulic, R. Carroll, B. L. Levine, C. H. June, and B. Dropulic. 2004. Efficient lentiviral vector-mediated control of HIV-1 replication in CD4 lymphocytes from diverse HIV+ infected patients grouped according to CD4 count and viral load. Mol Ther 9:902-913.
26. Leyva, F. J., J. J. Anzinger, J. P. McCoy, Jr., and H. S. Kruth. 2011. Evaluation of transduction efficiency in macrophage colony-stimulating factor differentiated human macrophages using HIV-1 based lentiviral vectors. BMC Biotechnol 11:13.
27. Page, K. A., N. R. Landau, and D. R. Littman. 1990. Construction and use of a human immunodeficiency virus vector for analysis of virus infectivity. Journal of virology 64:5270-5276.
28. Arya, S. K., C. Guo, S. F. Josephs, and F. Wong-Staal. 1985. Trans-activator gene of human T-lymphotropic virus type III (HTLV-III). Science 229:69-73.
29. Levy, D. N., G. M. Aldrovandi, O. Kutsch, and G. M. Shaw. 2004. Dynamics of HIV-1 recombination in its natural target cells. Proc Natl Acad Sci USA 101:4204-4209.
30. Trinite, B., C. N. Chan, C. S. Lee, S. Mahajan, Y. Luo, M. A. Muesing, J. M. Folkvord, M. Pham, E. Connick, and D. N. Levy. 2014. Suppression of Foxo1 activity and down-modulation of CD62L (L-selectin) in HIV-1 infected resting CD4 T cells. PLoS One 9:e110719.
31. Trinite, B., E. C. Ohlson, I. Voznesensky, S. P. Rana, C. N. Chan, S. Mahajan, J. Alster, S. A. Burke, D. Wodarz, and D. N. Levy. 2013. An HIV-1 replication pathway utilizing reverse transcription products that fail to integrate. J Virol 87:12701-12720.
32. O'Doherty, U., W. J. Swiggard, and M. H. Malim. 2000. Human immunodeficiency virus type 1 spinoculation enhances infection through virus binding. J Virol 74:10074-10080.
33. Plesa, G., J. Dai, C. Baytop, J. L. Riley, C. H. June, and U. O'Doherty. 2007. Addition of deoxynucleosides enhances human immunodeficiency virus type 1 integration and 2LTR formation in resting CD4+ T cells. J Virol 81:13938-13942.
34. Korin, Y. D., and J. A. Zack. 1999. Nonproductive human immunodeficiency virus type 1 infection in nucleoside-treated G0 lymphocytes. Journal of Virology 73:6526-6532.
35. Yang, H., E. Yorke, G. Hancock, G. Clutton, N. Sande, B. Angus, R. Smyth, J. Mak, and L. Dorrell. 2013. Improved quantification of HIV-1-infected CD4+ T cells using an optimised method of intracellular HIV-1 gag p24 antigen detection. Journal of immunological methods 391:174-178.
36. Liszewski, M. K., J. J. Yu, and U. O'Doherty. 2009. Detecting HIV-1 integration by repetitive-sampling Alu-gag PCR. Methods 47:254-260.
37. Boom, R., C. J. Sol, M. M. Salimans, C. L. Jansen, P. M. Wertheim-van Dillen, and J. van der Noordaa. 1990. Rapid and simple method for purification of nucleic acids. Journal of Clinical Microbiology 28:495-503.
38. Pasternak, A. O., K. W. Adema, M. Bakker, S. Jurriaans, B. Berkhout, M. Cornelissen, and V. V. Lukashov. 2008. Highly sensitive methods based on seminested real-time reverse transcription-PCR for quantitation of human immunodeficiency virus type 1 unspliced and multiply spliced RNA and proviral DNA. Journal of Clinical Microbiology 46:2206-2211.
39. Swiggard, W. J., C. Baytop, J. J. Yu, J. Dai, C. Li, R. Schretzenmair, T. Theodosopoulos, and U. O'Doherty. 2005. Human immunodeficiency virus type 1 can establish latent infection in resting CD4+ T cells in the absence of activating stimuli. J Virol 79:14179-14188.
40. Korin, Y. D., and J. A. Zack. 1998. Progression to the G1b phase of the cell cycle is required for completion of human immunodeficiency virus type 1 reverse transcription in T cells. Journal of Virology 72:3161-3168.
41. Baldauf, H. M., X. Pan, E. Erikson, S. Schmidt, W. Daddacha, M. Burggraf, K. Schenkova, I. Ambiel, G. Wabnitz, T. Gramberg, S. Panitz, E. Flory, N. R. Landau, S. Sertel, F. Rutsch, F. Lasitschka, B. Kim, R. Konig, O. T. Fackler, and O. T. Keppler. 2012. SAMHD1 restricts HIV-1 infection in resting CD4(+) T cells. Nat Med 18:1682-1687.
42. Lahouassa, H., W. Daddacha, H. Hofmann, D. Ayinde, E. C. Logue, L. Dragin, N. Bloch, C. Maudet, M. Bertrand, T. Gramberg, G. Pancino, S. Priet, B. Canard, N. Laguette, M. Benkirane, C. Transy, N. R. Landau, B. Kim, and F. Margottin-Goguet. 2012. SAMHD1 restricts the replication of human immunodeficiency virus type 1 by depleting the intracellular pool of deoxynucleoside triphosphates. Nat Immunol 13:223-228.
43. Stefanova, I., J. R. Dorfman, and R. N. Germain. 2002. Self-recognition promotes the foreign antigen sensitivity of naive T lymphocytes. Nature 420:429-434.
44. Ochsenbauer, C., T. G. Edmonds, H. Ding, B. F. Keele, J. Decker, M. G. Salazar, J. F. Salazar-Gonzalez, R. Shattock, B. F. Haynes, G. M. Shaw, B. H. Hahn, and J. C. Kappes. 2012. Generation of transmitted/founder HIV-1 infectious molecular clones and characterization of their replication capacity in CD4 T lymphocytes and monocyte derived macrophages. Journal of virology 86:2715-2728.
45. Das, M., J. W. Riess, P. Frankel, E. Schwartz, R. Bennis, H. B. Hsieh, X. Liu, J. C. Ly, L. Zhou, J. J. Nieva, H. A. Wakelee, and R. H. Bruce. 2012. ERCC1 expression in circulating tumor cells (CTCs) using a novel detection platform correlates with progression-free survival (PFS) in patients with metastatic non-small-cell lung cancer (NSCLC) receiving platinum chemotherapy. Lung Cancer 77:421-426.
46. Garcia, J. V., and A. D. Miller. 1991. Serine phosphorylation-independent downregulation of cell-surface CD4 by nef. Nature 350:508-511.
47. Rhee, S. S., and J. W. Marsh. 1994. Human immunodeficiency virus type 1 Nef induced down-modulation of CD4 is due to rapid internalization and degradation of surface CD4. Journal of virology 68:5156-5163.
48. Chen, B. K., R. T. Gandhi, and D. Baltimore. 1996. CD4 down-modulation during infection of human T cells with human immunodeficiency virus type 1 involves independent activities of vpu, env, and nef. J Virol 70:6044-6053.
49. Wildum, S., M. Schindler, J. Munch, and F. Kirchhoff. 2006. Contribution of Vpu, Env, and Nef to CD4 down-modulation and resistance of human immunodeficiency virus type 1-infected T cells to super infection. Journal of virology 80:8047-8059.
50. Stevenson, M., C. Meier, A. M. Mann, N. Chapman, and A. Wasiak. 1988. Envelope glycoprotein of HIV induces interference and cytolysis resistance in CD4+ cells: mechanism for persistence in AIDS. Cell 53:483-496.
51. Geleziunas, R., S. Bour, and M. A. Wainberg. 1994. Cell surface down-modulation of CD4 after infection by HIV-1. Faseb J 8:593-600.
52. Willey, R. L., F. Maldarelli, M. A. Martin, and K. Strebel. 1992. Human immunodeficiency virus type 1 Vpu protein induces rapid degradation of CD4. Journal of Virology 66:7193-7200.
53. Aiken, C., J. Konner, N. R. Landau, M. E. Lenburg, and D. Trono. 1994. Nef induces CD4 endocytosis: requirement for a critical dileucine motif in the membrane proximal CD4 cytoplasmic domain. Cell 76:853-864.
54. Munch, J., D. Rajan, M. Schindler, A. Specht, E. Rucker, F. J. Novembre, E. Nerrienet, M. C. Muller-Trutwin, M. Peeters, B. H. Hahn, and F. Kirchhoff. 2007. Nef-mediated enhancement of virion infectivity and stimulation of viral replication are fundamental properties of primate lentiviruses. Journal of virology 81:13852-13864.
55. Spina, C. A., J. C. Guatelli, and D. D. Richman 1995. Establishment of a stable, inducible form of human immunodeficiency virus type 1 DNA in quiescent CD4 lymphocytes in vitro. Journal of Virology 69:2877-2988.
56. Mohammadi, P., J. di Iulio, M. Munoz, R. Martinez, I. Bartha, M. Cavassini, C. Thorball, J. Fellay, N. Beerenwinkel, A. Ciuffi, and A. Telenti. 2014. Dynamics of HIV latency and reactivation in a primary CD4+ T cell model. PLoS pathogens 10:e1004156.
57. Wu, Y., and J. W. Marsh. 2001. Selective transcription and modulation of resting T cell activity by preintegrated HIV DNA. Science 293:1503-1506.
58. Cullen, B. R., and M. H. Malim. 1990. Regulation of HIV-1 gene expression. Nucleic Acids and Molecular Biology 4:176-184.
59. Kutsch, O., E. N. Benveniste, G. M. Shaw, and D. N. Levy. 2002. Direct and quantitative single-cell analysis of human immunodeficiency virus type 1 reactivation from latency. J Virol 76:8776-8786.
60. Pasternak, A. O., S. Jurriaans, M. Bakker, J. M. Prins, B. Berkhout, and V. V. Lukashov. 2009. Cellular levels of HIV unspliced RNA from patients on combination antiretroviral therapy with undetectable plasma viremia predict the therapy outcome. PLoS One 4:e8490.
61. Eisele, E., and R. F. Siliciano. 2012. Redefining the viral reservoirs that prevent HIV-1 eradication. Immunity 37:377-388.
62. Piguet, V., O. Schwartz, S. Le Gall, and D. Trono. 1999. The downregulation of CD4 and MHC-I by primate lentiviruses: a paradigm for the modulation of cell surface receptors. Immunol Rev 168:51-63.
63. Glushakova, S., J. Munch, S. Carl, T. C. Greenough, J. L. Sullivan, L. Margolis, and F. Kirchhoff. 2001. CD4 down-modulation by human immunodeficiency virus type 1 Nef correlates with the efficiency of viral replication and with CD4(+) T-cell depletion in human lymphoid tissue ex vivo. Journal of virology 75:10113-10117.
64. Lassen, K. G., J. R. Bailey, and R. F. Siliciano. 2004. Analysis of human immunodeficiency virus type 1 transcriptional elongation in resting CD4+ T cells in vivo. J Virol 78:9105-9114.
65. Wei, D. G., V. Chiang, E. Fyne, M. Balakrishnan, T. Barnes, M. Graupe, J. Hesselgesser, A. Irrinki, J. P. Murry, G. Stepan, K. M. Stray, A. Tsai, H. Yu, J. Spindler, M. Kearney, C. A. Spina, D. McMahon, J. Lalezari, D. Sloan, J. Mellors, R. Geleziunas, and T. Cihlar. 2014. Histone Deacetylase Inhibitor Romidepsin Induces HIV Expression in CD4 T Cells from Patients on Suppressive Antiretroviral Therapy at Concentrations Achieved by Clinical Dosing. PLoS pathogens 10:e1004071.
66. Cillo, A. R., M. D. Sobolewski, R. J. Bosch, E. Fyne, M. Piatak, Jr., J. M. Coffin, and J. W. Mellors. 2014. Quantification of HIV-1 latency reversal in resting CD4+ T cells from patients on suppressive antiretroviral therapy. Proc Natl Acad Sci USA.
67. Spina, C. A., J. Anderson, N. M. Archin, A. Bosque, J. Chan, M. Famiglietti, W. C. Greene, A. Kashuba, S. R. Lewin, D. M. Margolis, M. Mau, D. Ruelas, S. Saleh, K. Shirakawa, R. F. Siliciano, A. Singhania, P. C. Soto, V. H. Terry, E. Verdin, C. Woelk, S. Wooden, S. Xing, and V. Planelles. 2013. An in-depth comparison of latent HIV-1 reactivation in multiple cell model systems and resting CD4+ T cells from aviremic patients. PLoS pathogens 9:e1003834.
68. Cameron, P. U., S. Saleh, G. Sallmann, A. Solomon, F. Wightman, V. A. Evans, G. Boucher, E. K. Haddad, R. P. Sekaly, A. N. Harman, J. L. Anderson, K. L. Jones, J. Mak, A. L. Cunningham, A. Jaworowski, and S. R. Lewin. 2011. Establishment of HIV-1 latency in resting CD4+ T cells depends on chemokine-induced changes in the actin cytoskeleton. Proc Natl Acad Sci USA 107:16934-16939.
69. Saleh, S., A. Solomon, F. Wightman, M. Xhilaga, P. U. Cameron, and S. R. Lewin. 2007. CCR7 ligands CCL19 and CCL21 increase permissiveness of resting memory CD4+ T cells to HIV-1 infection: a novel model of HIV-1 latency. Blood 110:4161-4164.
70. Chavez, L., V. Calvanese, and E. Verdin. 2015. HIV Latency Is Established Directly and Early in Both Resting and Activated Primary CD4 T Cells. PLoS Pathog 11:e1004955.
71. Vatakis, D. N., G. Bristol, T. A. Wilkinson, S. A. Chow, and J. A. Zack. 2007. Immediate activation fails to rescue efficient human immunodeficiency virus replication in quiescent CD4+ T cells. J Virol 81:3574-3582.
72. Lucera, M. B., C. A. Tilton, H. Mao, C. Dobrowolski, C. O. Tabler, A. A. Haqqani, J. Karn, and J. C. Tilton. 2014. The histone deacetylase inhibitor vorinostat (SAHA) increases the susceptibility of uninfected CD4+ T cells to HIV by increasing the kinetics and efficiency of postentry viral events. J Virol 88:10803-10812.
73. Chomont, N., M. El-Far, P. Ancuta, L. Trautmann, F. A. Procopio, B. Yassine-Diab, G. Boucher, M. R. Boulassel, G. Ghattas, J. M. Brenchley, T. W. Schacker, B. J. Hill, D. C. Douek, J. P. Routy, E. K. Haddad, and R. P. Sekaly. 2009. HIV reservoir size and persistence are driven by T cell survival and homeostatic proliferation. Nat Med 15:893-900.
74. Ostrowski, M. A., T.-W. Chun, S. J. Justement, I. Motola, M. A. Spinelli, J. Adelsberger, L. A. Ehler, S. B. Mizell, C. W. Hallahan, and A. S. Fauci. 1999. Both memory and CD45RA(+)/CD62L(+) naive CD4(+) T cells are infected in human immunodeficiency type 1-infected individuals. Journal of Virology 73:6430-6435.
75. Dai, J., L. M. Agosto, C. Baytop, J. J. Yu, M. J. Pace, M. K. Liszewski, and U. O'Doherty. 2009. Human immunodeficiency virus integrates directly into naive resting CD4+ T cells but enters naive cells less efficiently than memory cells. J Virol 83:4528-4537.
76. Yukl, S. A., E. Sinclair, M. Somsouk, P. W. Hunt, L. Epling, M. Killian, V. Girling, P. Li, D. V. Havlir, S. G.

Deeks, J. K. Wong, and H. Hatano. 2014. A comparison of methods for measuring rectal HIV levels suggests that HIV DNA resides in cells other than CD4+ T cells, including myeloid cells. AIDS 28:439-442.

77. Iyer, S. R., D. Yu, A. Biancotto, L. B. Margolis, and Y. Wu. 2009. Measurement of human immunodeficiency virus type 1 preintegration transcription by using Rev-dependent Rev-CEM cells reveals a sizable transcribing DNA population comparable to that from proviral templates. J Virol 83:8662-8673.

78. Merzouki, A., P. Patel, S. Cassol, M. Ennaji, P. Tailor, F. R. Turcotte, M. O'Shaughnessy, and M. Arella. 1995. HIV-1 gp120/160 expressing cells upregulate HIV-1 LTR directed gene expression in a cell line transfected with HIV-1 LTR-reporter gene constructs. Cell Mol Biol 41:445-452.

79. Imamichi, H., V. Natarajan, J. W. Adelsberger, C. A. Rehm, R. A. Lempicki, B. Das, A. Hazen, T. Imamichi, and H. C. Lane. 2014. Lifespan of effector memory CD4+ T cells determined by replication-incompetent integrated HIV-1 provirus. AIDS.

80. Chun, T. W., D. C. Nickle, J. S. Justement, D. Large, A. Semerjian, M. E. Curlin, M. A. O'Shea, C. W. Hallahan, M. Daucher, D. J. Ward, S. Moir, J. I. Mullins, C. Kovacs, and A. S. Fauci. 2005. HIV-infected individuals receiving effective antiviral therapy for extended periods of time continually replenish their viral reservoir. J Clin Invest 115:3250-3255.

81. Lambotte, O., M. L. Chaix, B. Gubler, N. Nasreddine, C. Wallon, C. Goujard, C. Rouzioux, Y. Taoufik, and J. F. Delfraissy. 2004. The lymphocyte HIV reservoir in patients on long-term HAART is a memory of virus evolution. AIDS 18:1147-1158.

82. Coiras, M., M. R. Lopez-Huertas, M. Perez-Olmeda, and J. Alcami. 2009. Understanding HIV-1 latency provides clues for the eradication of long-term reservoirs. Nat Rev Microbiol 7:798-812.

83. Hellerstein, M., M. B. Hanley, D. Cesar, S. Siler, C. Papageorgopoulos, E. Wieder, D. Schmidt, R. Hoh, R. Neese, D. Macallan, S. Deeks, and J. M. McCune. 1999. Directly measured kinetics of circulating T lymphocytes in normal and HIV-1-infected humans. Nat Med 5(1):83-89.

84. Murray, J. M., J. J. Zaunders, K. L. McBride, Y. Xu, M. Bailey, K. Suzuki, D. A. Cooper, S. Emery, A. D. Kelleher, K. K. Koelsch, and P. S. Team. 2014. HIV DNA subspecies persist in both activated and resting memory CD4+ T cells during antiretroviral therapy. Journal of virology 88:3516-3526.

85. Archin, N. M., A. L. Liberty, A. D. Kashuba, S. K. Choudhary, J. D. Kuruc, A. M. Crooks, D. C. Parker, E. M. Anderson, M. F. Kearney, M. C. Strain, D. D. Richman, M. G. Hudgens, R. J. Bosch, J. M. Coffin, J. J. Eron, D. J. Hazuda, and D. M. Margolis. 2012. Administration of vorinostat disrupts HIV-1 latency in patients on anti-retroviral therapy. Nature 487:482-485.

86. Lassen, K. G., K. X. Ramyar, J. R. Bailey, Y. Zhou, and R. F. Siliciano. 2006. Nuclear retention of multiply spliced HIV-1 RNA in resting CD4+ T cells. PLoS Pathog 2:e68.

87. Archin, N. M., R. Bateson, M. Tripathy, A. M. Crooks, K. H. Yang, N. P. Dahl, M. F. Kearney, E. M. Anderson, J. M. Coffin, M. C. Strain, D. D. Richman, K. R. Robertson, A. D. Kashuba, R. J. Bosch, D. J. Hazuda, J. D. Kuruc, J. J. Eron, and D. M. Margolis. 2014. HIV-1 Expression within Resting CD4 T-Cells Following Multiple Doses of Vorinostat. J Infect Dis.

88. Jones, R. B., R. O'Connor, S. Mueller, M. Foley, G. L. Szeto, D. Karel, M. Lichterfeld, C. Kovacs, M. A. Ostrowski, A. Trocha, D. J. Irvine, and B. D. Walker. 2014. Histone deacetylase inhibitors impair the elimination of HIV-infected cells by cytotoxic T-lymphocytes. PLoS Pathog 10:e1004287.

89. Shan, L., K. Deng, N. S. Shroff, C. M. Durand, S. A. Rabi, H.-C. Yang, H. Zhang, J. B. Margolick, J. N. Blankson, and R. F. Siliciano. 2012. Stimulation of HIV-1-specific cytolytic T lymphocytes facilitates elimination of latent viral reservoir after virus reactivation Immunity 36:491-501.

90. Buckheit, R. W., 3rd, R. F. Siliciano, and J. N. Blankson. 2013. Primary CD8+ T cells from elite suppressors effectively eliminate non-productively HIV-1 infected resting and activated CD4+ T cells. Retrovirology 10:68.

91. Migueles, S. A., C. M. Osborne, C. Royce, A. A. Compton, R. P. Joshi, K. A. Weeks, J. E. Rood, A. M. Berkley, J. B. Sacha, N. A. Cogliano-Shutta, M. Lloyd, G. Roby, R. Kwan, M. McLaughlin, S. Stallings, C. Rehm, M. A. O'Shea, J. Mican, B. Z. Packard, A. Komoriya, S. Palmer, A. P. Wiegand, F. Maldarelli, J. M. Coffin, J. W. Mellors, C. W. Hallahan, D. A. Follman, and M. Connors. 2008. Lytic granule loading of CD8+ T cells is required for HIV-infected cell elimination associated with immune control. Immunity 29:1009-1021.

The invention encompasses all combinations of recited particular and preferred embodiments. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method to detect latent human immunodeficiency virus (HIV) reservoirs that express HIV proteins in a patient suspected of having latent HIV infection, the method comprising identifying, by performing optical scanning, Group specific antigen (Gag)+ CD4 downregulated cells in a cell sample of the patient, wherein the Gag+ CD4 downregulated cells detect a latent HIV reservoir that expresses HIV proteins in the patient; wherein the optical scanning is fiber-optic array scanning.

2. The method of claim 1 wherein the patient is on anti-retroviral therapy (ART).

3. The method of claim 1 wherein the patient had been on ART for at least one or two years.

4. The method of claim 1 wherein the patient has experimentally undetectable viral load.

5. The method of claim 1 wherein the sample comprises peripheral blood mononuclear cells (PBMCs) of the patient, adhered to a slide, fixed and permeabilized and stained for CD4 and intracellular GAG.

6. The method of claim 1 further comprising assigning positional coordinates to one or more of the Gag+ CD4 downregulated cells.

7. The method of claim 1 further comprising isolating one or more of the Gag+ CD4 downregulated cells.

8. The method of claim 1 further comprising a secondary analysis of one or more of the Gag+ CD4 downregulated cells that is quantifying multiplexed fluorescent markers by fluorescent microscopy.

9. The method of claim 1 further comprising a secondary analysis of one or more of the Gag+ CD4 downregulated cells that is genetic analysis of the cell or of the HIV.

10. The method of claim 1 further comprising a secondary analysis of one or more of the Gag+ CD4 downregulated cells that identify one or more additional expressed proteins selected from the group consisting of additional HIV proteins and cellular surface receptors that characterize the cells phenotype.

11. The method of claim 1 comprising mounting a slide comprising the cell sample on a fiber optic array scanner and fluorescent imaging the cells.

12. The method of claim 11 wherein the fiber-optic array scanner comprises:
- an imager stage having a planar surface for supporting a sample comprising the slide;
- a bifurcated light path having two fiber optic bundles, each bundle having a first end arranged to define an input aperture for viewing the sample on the imager stage, and a distal bundle end arranged to define an output aperture disposed away from the imager stage;
- a scanning source arranged to scan a beam along a path that is perpendicular to the sample on the imager stage and closely adjacent to both bundles of the bifurcated light path such that a substantially circular spot of illumination provided by the scanning source on the imager stage sample provides a light signal at least a portion of which is received by the input aperture of each bundle and transmitted via the bifurcated light path to the output aperture;
- a photodetector arranged to detect the light signal at the distal end; and
- a processor that processes the light signal detected by the photodetector.

13. The method of claim 11 comprising:
- supplying a substantially circular beam of radiation perpendicular to the sample;
- maintaining the perpendicular direction of the radiation beam as it sweeps along a scan path on the sample;
- reflecting at least some light produced by beam interaction with the sample in a direction away from the sample;
- collecting light produced by beam interaction with the sample in at least one proximate element of an array of fiber optic first ends;
- detecting collected light at a selected output region; and
- coordinating sweeping, moving and detecting to generate an array of picture elements representative of at least a portion of the sample.

* * * * *